United States Patent
Nagano et al.

(10) Patent No.: US 8,178,669 B2
(45) Date of Patent: May 15, 2012

(54) FLUORESCENT PROBE FOR PEROXYNITRITE

(75) Inventors: Tetsuo Nagano, Tokyo (JP); Yasuteru Urano, Kanagawa (JP); Tasuku Ueno, Saitama (JP)

(73) Assignee: The University of Tokyo, Tokyo (JP)

( * ) Notice: Subject to any disclaimer, the term of this patent is extended or adjusted under 35 U.S.C. 154(b) by 127 days.

(21) Appl. No.: 12/093,479

(22) PCT Filed: Nov. 14, 2006

(86) PCT No.: PCT/JP2006/322599
§ 371 (c)(1), (2), (4) Date: Jun. 15, 2009

(87) PCT Pub. No.: WO2007/055364
PCT Pub. Date: May 18, 2007

(65) Prior Publication Data
US 2009/0258434 A1  Oct. 15, 2009

Related U.S. Application Data

(60) Provisional application No. 60/735,815, filed on Nov. 14, 2005.

(51) Int. Cl.
*C07F 5/02* (2006.01)
(52) U.S. Cl. .......................................... 544/229
(58) Field of Classification Search .................. 544/229
See application file for complete search history.

(56) References Cited

U.S. PATENT DOCUMENTS

| | | | |
|---|---|---|---|
| 6,001,999 | A | 12/1999 | Wolfbeis et al. |
| 2003/0153027 | A1 | 8/2003 | Nagano et al. |
| 2006/0275912 | A1 | 12/2006 | Nagano et al. |

FOREIGN PATENT DOCUMENTS

| | | |
|---|---|---|
| EP | 1 604 994 | 12/2005 |
| JP | 10-338695 | 12/1998 |
| JP | 11-5796 | 1/1999 |
| JP | 2003-277385 | 10/2003 |
| JP | 2005-053900 | 3/2005 |
| WO | 01/64664 | 9/2001 |
| WO | 2004/076466 | 9/2004 |

OTHER PUBLICATIONS

Ueno et al. Mechanism-Based Molecular Design of Highly Selective Fluorescence Probes for Nitrative Stress. 2006, Journal of the American Chemical Society, 128, 10640-10641 (supporting information included).*

\* cited by examiner

*Primary Examiner* — James O Wilson
*Assistant Examiner* — Brian McDowell
(74) *Attorney, Agent, or Firm* — Greenblum & Bernstein, PLC

(57) ABSTRACT

A compound represented by the following general formula (I):

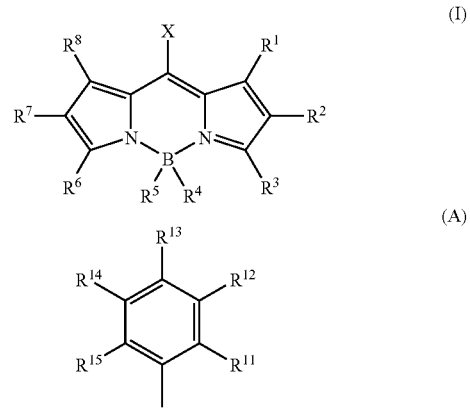

$\{R^1, R^3, R^6$ and $R^8$ are methyl groups and the like, $R^2$ and $R^7$ are cyano groups and the like, $R^4$ and $R^5$ are fluorine atoms and the like, and X is a group represented by the formula (A) [$R^{11}$ is a monocarboxy-substituted $C_{1-8}$ alkoxy group and the like, $R^{12}$, $R^{14}$ and $R^{15}$ are hydrogen atoms and the like, and $R^{13}$ is hydroxy group and the like], provided that the combination of the aforementioned substituents is such a combination that the compound represented by the formula (I) can be substantially non-fluorescent before reacting with peroxynitrite, and the compound represented by the formula (I) in which the group represented by the formula (A) is nitrated after reacting with peroxynitrite can be substantially highly fluorescent$\}$, or a salt thereof, which is useful as a fluorescent probe for peroxynitrite measurement.

12 Claims, 3 Drawing Sheets

[Fig. 1]
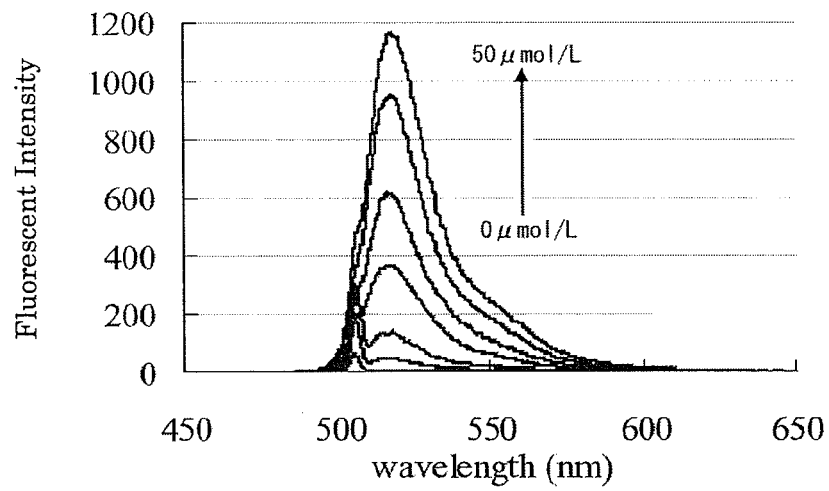
[Fig. 2]
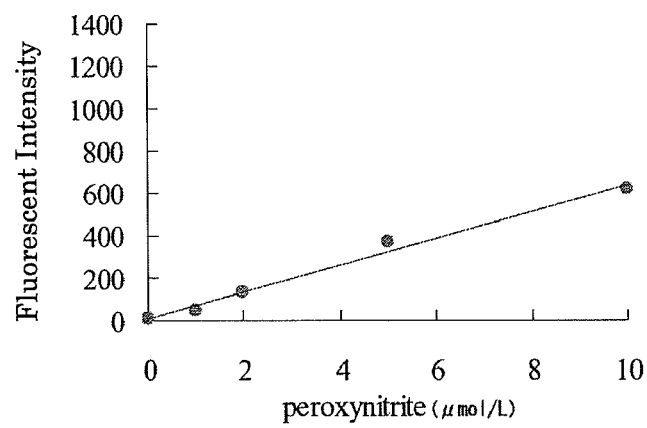
[Fig. 3]
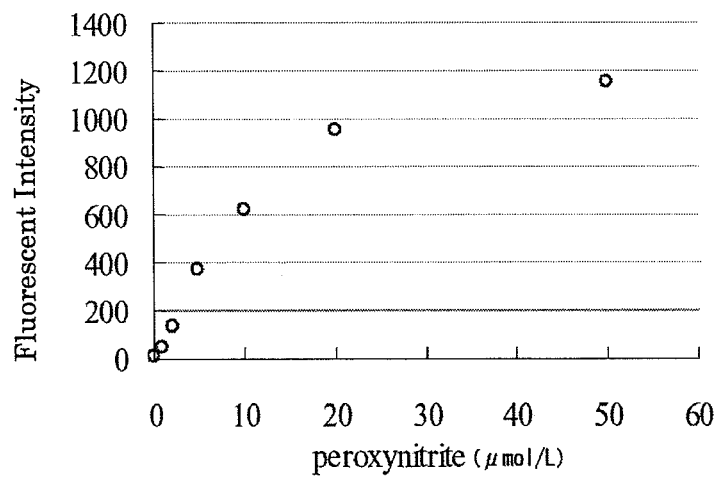

[Fig.4]
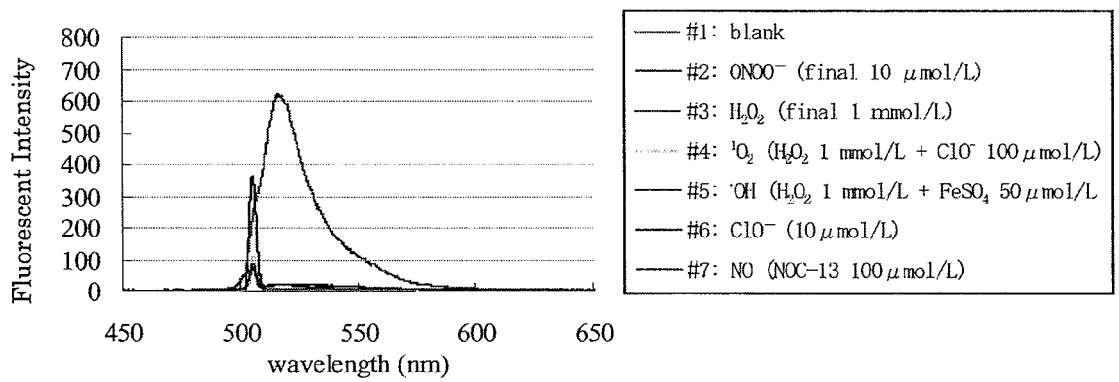
[Fig.5]
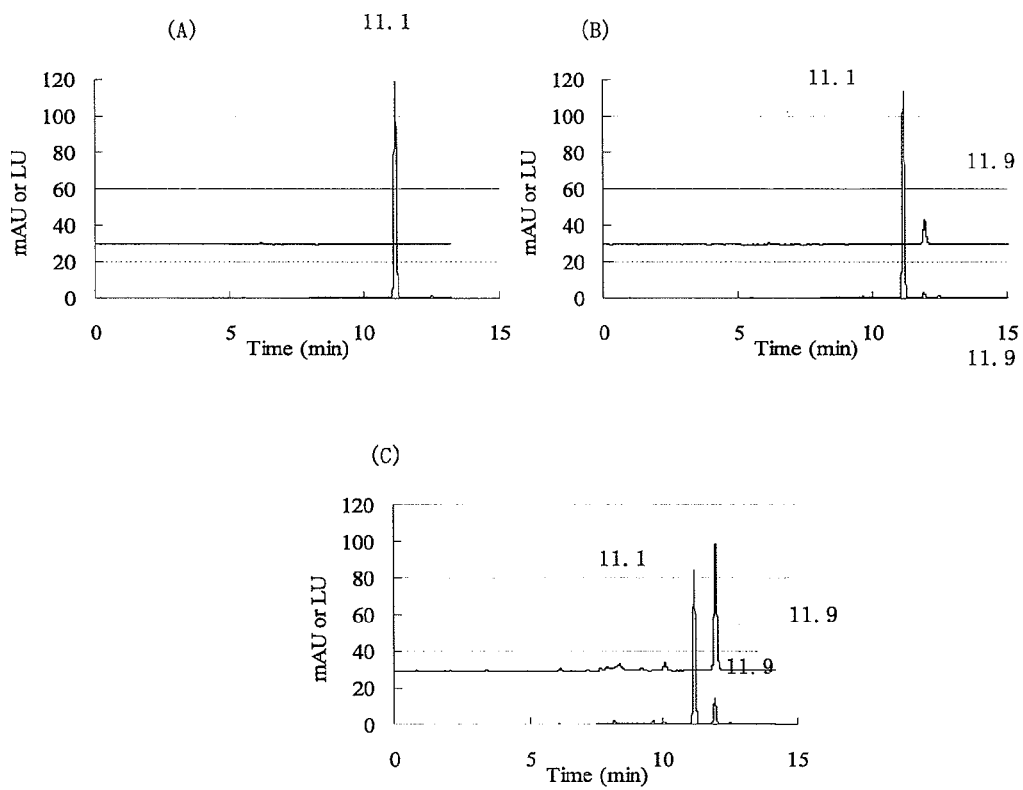

[Fig.6]
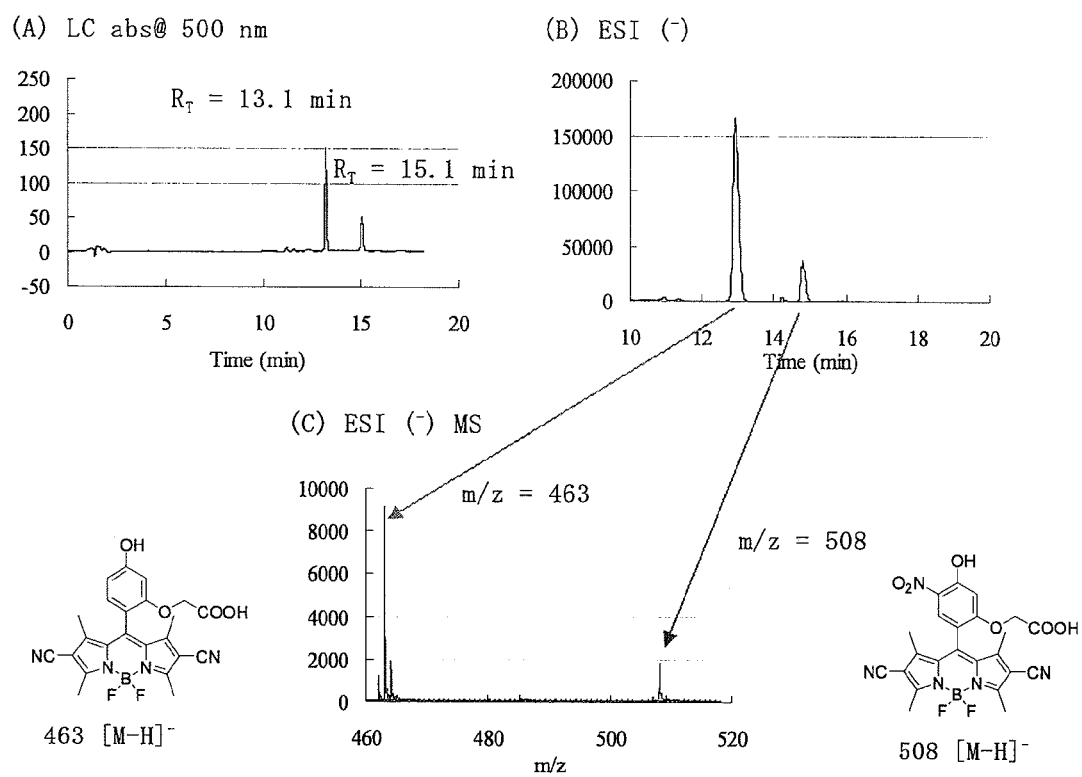
[Fig.7]
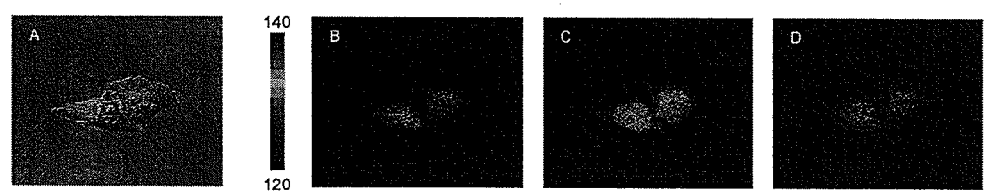

FLUORESCENT PROBE FOR PEROXYNITRITE

TECHNICAL FIELD

The present invention relates to a peroxynitrite fluorescent probe. More specifically, the present invention relates to a novel compound which per se is substantially non-fluorescent, but after reacting with peroxynitrite and thereby being nitrated, emits intense fluorescence, and a method for measuring peroxynitrite by using the compound.

BACKGROUND ART

In recent years, it has been revealed that nitrogen monoxide (NO) is an endogenous physiologically active substance having various functions responsible for, for example, blood vessel relaxation, regulation of nervous signal transduction, control of cell death, carcinogenesis, and the like. It is considered that nitrogen monoxide itself has relatively weak reactivity, and is converted to various reactive nitrogen species (RNS) having high reactivity by reactions with various active oxygen species simultaneously produced in living bodies, metal ions and the like to cause cell injury. More recently, there are many reports teaching that various signal transduction routes are regulated by modification of proteins with RNS, and it is also being revealed that RNS including peroxynitrite participate in various diseases by giving the DNAs damage. Therefore, not only nitrogen monoxide but RNS have been attracting a great deal of attention.

Peroxynitrite (ONOO⁻) is a typical substance among RNS, and is produced by a reaction of nitrogen monoxide and superoxide. Reaction rate of this production reaction is mostly limited by diffusion, and when superoxide produced by NADPH oxidase or the like and nitrogen monoxide produced by nitrogen monoxide synthetase (NOS) coexist, peroxynitrite is immediately produced. Peroxynitrite has high oxidation ability, for example, it achieves nitration of an aromatic ring, and has characteristic reactivities such as, for example, efficient nitration of tyrosine. Recent reports have pointed out that phosphorylation of tyrosine is inhibited by nitration of tyrosine, and thus peroxynitrite has an important effect on signal transduction systems such as MAPK and PI3K/Akt cascades.

Examples of the methods for detecting peroxynitrite developed so far include (1) a method of detecting 8-nitroguanine produced by nitration of guanine which is a DNA base, or nitrotyrosine produced by nitration of tyrosine by HPLC or immunostaining using an antibody, and (2) a method of detecting singlet oxygen produced by reaction of peroxynitrite and hydrogen peroxide on the basis of light emission at 1.3 μm. Although the method (1) achieves high specificity and has been widely used, the method has a problem in that peroxynitrite cannot be detected in real time by applying the method to a living cell system, because HPLC analysis or staining with antibodies should be performed. In addition to the aforementioned two methods, (3) a chemiluminescence method using luminol, and (4) a fluorometric detection method using a fluorescence probe to detect overall active oxygen species such as 2′,7′-dichlorodihydrofluorescein (DCFH) have been used. However, these methods fail to achieve specificity, and therefore reliable detection cannot be expected even if various inhibitors are used. For example, in the method (4), DCFH reacts with both of nitrogen monoxide and superoxide to give an increase in fluorescence, and therefore it is impossible to distinguish whether peroxynitrite is detected, or nitrogen monoxide or superoxide is detected.

Arylated fluorescein derivatives are known to be useful fluorescent probes for measuring active oxygen (International Patent Publication WO01/64664). Moreover, these fluorescein derivatives are known to be useful as fluorescent probes which do not react with nitrogen monoxide and superoxide which are precursors of peroxynitrite, and thus enables measurement of peroxynitrite while distinguishing it from those precursors (International Patent Publication WO2004/40296). However, these fluorescein derivatives have a problem that they also react with reactive oxygen species (ROS) such as hypochlorite ion and hydroxyl radical, and thus are not capable of achieving specific detection solely of peroxynitrite while distinguishing it from other ROS. Therefore, it has been desired to develop a fluorescent probe which can highly selectively visualize peroxynitrite in a living cell or tissue.

DISCLOSURE OF THE INVENTION

Object to be Achieved by the Invention

An object of the present invention is to provide a fluorescent probe which achieves highly selective measurement of peroxynitrite. The object of the present invention is, in particular, to provide a highly selective peroxynitrite-fluorescent probe applicable to bioimaging methods.

Means for Achieving the Object

The inventors of the present invention conducted various researches to achieve the foregoing object. As a result, they found that the substantially non-fluorescent compounds represented by the following general formula (I), having fluorescence chromophores of indacene derivatives (Japanese Patent Laid-Open Publication (KOKAI) Nos. 10-338695 and 11-5796), were useful as probes for highly selective measurement of peroxynitrite; because they gave highly fluorescent nitro compounds only through nitration of phenol, a typical chemical reaction with peroxynitrite, whilst they did not give fluorescent compounds even if they reacted with highly reactive oxygen species such as hydroxyl radical and hypochlorite ion, or weakly active reactive oxygen species such as hydrogen peroxide and nitrogen monoxide, or reactive nitrogen species other than peroxynitrite under physiological conditions. The present invention was accomplished on the basis of the aforementioned finding.

The present invention thus provides a compound represented by the following general formula (I):

[Formula 1]

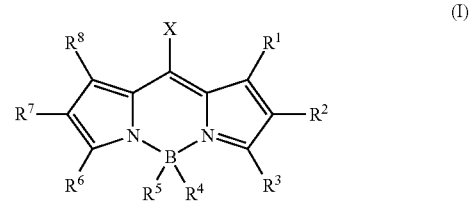

{wherein $R^1$, $R^2$, $R^3$, $R^6$, $R^7$ and $R^8$ independently represent hydrogen atom, a $C_{1-8}$ alkyl group which may be substituted, an aryl group which may be substituted, a vinyl group which may be substituted, a thienyl group which may be substituted, or a pyrrolyl group which may be substituted, or represent an electron withdrawing group selected from the group consisting of cyano group, carboxy group and an alkyloxycarbonyl group which may be substituted, provided that 2 to 6 groups among $R^1$, $R^2$, $R^3$, $R^6$, $R^7$ and $R^8$ represent an electron withdrawing group selected from cyano group, carboxy group and a $C_{1-8}$ alkyloxycarbonyl group which may be substituted, $R^4$ and $R^5$ independently represent a halogen atom, a $C_{1-8}$ alkyl group which may be substituted, or a $C_{1-8}$ alkoxy group which may be substituted, and X represents a group represented by the following formula (A):

[Formula 2]

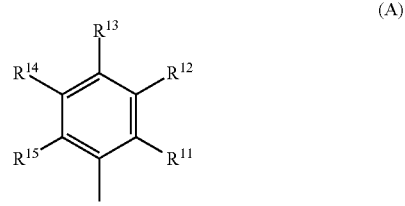

[wherein $R^{11}$, $R^{12}$, $R^{13}$, $R^{14}$ and $R^{15}$ independently represent hydrogen atom, a $C_{1-8}$ alkyl group which may be substituted, a $C_{1-8}$ alkoxy group which may be substituted, hydroxyhydroxy group, an amino group (the amino group may be primary, secondary or tertiary amino group), thiol group or selenol group, provided that 2 to 3 groups among $R^{11}$, $R^{12}$, $R^{13}$, $R^{14}$ and $R^{15}$ represent a $C_{1-8}$ alkoxy group which may be substituted, hydroxyhydroxy group, an amino group (the amino group may be primary, secondary or tertiary amino group), thiol group or selenol group, but all the groups do not simultaneously represent a $C_{1-8}$ alkoxy group which may be substituted],
provided that the combination of the aforementioned substituents is such a combination that the compound represented by the formula (I) can be substantially non-fluorescent before reacting with peroxynitrite, and the compound represented by the formula (I) in which the group represented by the formula (A) is nitrated after reacting with peroxynitrite can be substantially highly fluorescent}, or a salt thereof.

According to a preferred embodiment of the aforementioned invention, there is provided the compound represented by the general formula (I) or a salt thereof, wherein the combination of the substituents of $R^1$, $R^2$, $R^3$, $R^6$, $R^7$ and $R^8$ is a combination giving substantially low electron density to the aforementioned indacene ring moiety so that the compound represented by the formula (I) can be substantially non-fluorescent before reacting with peroxynitrite, the combination of the substituents of $R^{11}$, $R^{12}$, $R^{13}$, $R^{14}$ and $R^{15}$ is a combination giving substantially high electron density to the benzene ring represented by the formula (A), and further, the combination of the substituents of $R^{11}$, $R^{12}$, $R^{13}$, $R^{14}$ and $R^{15}$ in the formula (A) is a combination which maintains electron density of the aforementioned benzene ring to be sufficiently high so that the compound represented by the formula (I) wherein the group represented by the formula (A) is nitrated after reacting with peroxynitrite can be substantially highly fluorescent.

According to preferred embodiments of this invention, there are provided the compound, wherein, in the aforementioned general formula (I), $R^1$, $R^3$, $R^6$ and $R^8$ are methyl groups, $R^2$ and $R^7$ are cyano groups, $R^4$ and $R^5$ are fluorine atoms, and X is a group represented by the aforementioned formula (A) (wherein the substituents have the same meanings as those defined above); and the compound or a salt thereof, wherein, in the aforementioned general formula (I), $R^1$, $R^3$, $R^6$ and $R^8$ are methyl groups, $R^2$ and $R^7$ are cyano groups, $R^4$ and $R^5$ are fluorine atoms, and X is a group represented by the aforementioned formula (A) (wherein $R^{11}$ is a $C_{1-8}$ alkoxy group which may be substituted, $R^{12}$, $R^{14}$ and $R^{15}$ are hydrogen atoms, and $R^{13}$ is hydroxyhydroxy group). As the $C_{1-8}$ alkoxy group which may be substituted represented by $R^{11}$, methoxy group, ethoxy group, or carboxymethoxy group is preferred. Carboxymethoxy group is particularly preferred.

According to another preferred embodiment of the aforementioned invention, there is also provided a compound represented by the following general formula (II):

[Formula 3]

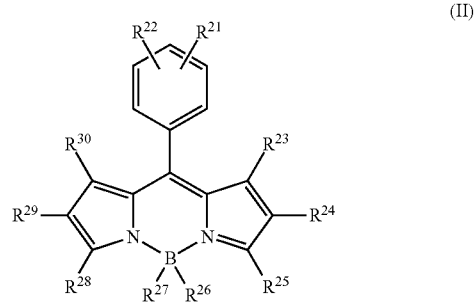

(wherein $R^{21}$ and $R^{22}$ independently represent a $C_{1-8}$ alkoxy group which may be substituted, hydroxy group, an amino group (the amino group may be primary, secondary or tertiary amino group), thiol group or selenol group, provided that both $R^{21}$ and $R^{22}$ do not simultaneously represent a $C_{1-8}$ alkoxy group which may be substituted, $R^{23}$, $R^{25}$, $R^{28}$ and $R^{30}$ represent a $C_{1-8}$ alkyl group which may be substituted, $R^{24}$ and $R^{29}$ represent an electron withdrawing group selected from the group consisting of cyano group, carboxy group and an alkyloxycarbonyl group which may be substituted, $R^{26}$ and $R^{27}$ independently represent a halogen atom, a $C_{1-8}$ alkyl group which may be substituted, or a $C_{1-8}$ alkoxy group which may be substituted), or a salt thereof.

According to a preferred embodiment of this invention, there is provided the compound or a salt thereof, wherein, in the aforementioned general formula (II), $R^{21}$ and $R^{22}$ consist of a combination of hydroxy group and a $C_{1-8}$ alkoxy group which may be substituted, $R^{23}$, $R^{25}$, $R^{28}$ and $R^{30}$ are $C_{1-8}$ alkyl groups which may be substituted, $R^{24}$ and $R^{29}$ are cyano groups, and $R^{26}$ and $R^{27}$ are fluorine atoms. According to a more preferred embodiment, there is provided the compound or a salt thereof, wherein, in the aforementioned general formula (II), $R^{21}$ and $R^{22}$ consist of a combination of hydroxy group and a $C_{1-4}$ alkoxy group or a mono-carboxy group-substituted $C_{1-4}$ alkoxy group, $R^{23}$, $R^{25}$, $R^{28}$ and $R^{30}$ are $C_{1-4}$ alkyl groups, $R^{24}$ and $R^{29}$ are cyano groups, and $R^{26}$ and $R^{27}$ are fluorine atoms.

From another aspect, there is provided a compound represented by the following general formula (III):

[Formula 4]

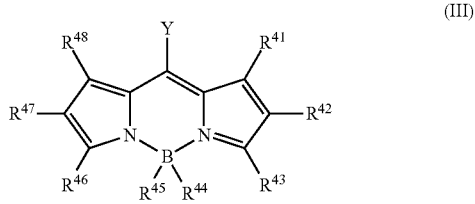

{wherein $R^{41}$, $R^{42}$, $R^{43}$, $R^{46}$, $R^{47}$ and $R^{48}$ independently represent hydrogen atom, a $C_{1-8}$ alkyl group which may be substituted, an aryl group which may be substituted, a vinyl group which may be substituted, a thienyl group which may be substituted, or a pyrrolyl group which may be substituted, or represent an electron withdrawing group selected from the group consisting of cyano group, carboxy group and an alkyloxycarbonyl group which may be substituted, provided that 2 to 6 groups among $R^{41}$, $R^{42}$, $R^{43}$, $R^{46}$, $R^{47}$ and $R^{48}$ represent an electron withdrawing group selected from cyano group, carboxy group and a $C_{1-8}$ alkyloxycarbonyl group which may be substituted, $R^{44}$ and $R^{45}$ independently represent a halogen atom, a $C_{1-8}$ alkyl group which may be substituted, or a $C_{1-8}$ alkoxy group which may be substituted, and Y represents a group represented by the following formula (B):

[Formula 5]

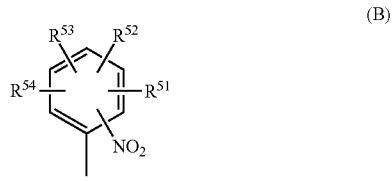

[wherein $R^{51}$, $R^{52}$, $R^{53}$ and $R^{54}$ independently represent hydrogen atom, a $C_{1-8}$ alkyl group which may be substituted, a $C_{1-8}$ alkoxy group which may be substituted, hydroxy group, an amino group (the amino group may be primary, secondary or tertiary amino group), thiol group or selenol group, provided that 2 to 3 groups among $R^{51}$, $R^{52}$, $R^{53}$ and $R^{54}$ represent a $C_{1-8}$ alkoxy group which may be substituted, hydroxy group, an amino group (the amino group may be primary, secondary or tertiary amino group), thiol group or selenol group, but all the groups do not simultaneously represent a $C_{1-8}$ alkoxy group which may be substituted], provided that the combination of the aforementioned substituents is such a combination that the compound represented by the formula (III) can be substantially highly fluorescent}, or a salt thereof.

According to a preferred embodiment of this invention, there is provided the aforementioned compound or a salt thereof, wherein the combination of the substituents of $R^{51}$, $R^{52}$, $R^{53}$ and $R^{54}$ is a combination which maintains electron density of the aforementioned benzene ring in the group represented by the formula (B) to be sufficiently high so that the compound represented by the formula (III) can be substantially highly fluorescent.

According to a preferred embodiment of this invention, there is provided the compound or a salt thereof, wherein, in the aforementioned general formula (III), $R^{41}$, $R^{43}$, $R^{46}$ and $R^{48}$ are methyl groups, $R^{42}$ and $R^{47}$ are cyano groups, $R^{44}$ and $R^{45}$ are fluorine atoms, and Y is a group represented by the formula (B) (in the formula (B), $R^{51}$ is a $C_{1-8}$ alkoxy group which may be substituted, $R^{52}$ and $R^{53}$ are hydrogen atoms, and $R^{54}$ is hydroxy group). As the $C_{1-8}$ alkoxy group which may be substituted represented by $R^{51}$, methoxy group, ethoxy group or carboxymethoxy group is preferred. Carboxymethoxy group is particularly preferred.

According to another preferred embodiment, there is provided a compound represented by the following general formula (IV):

[Formula 6]

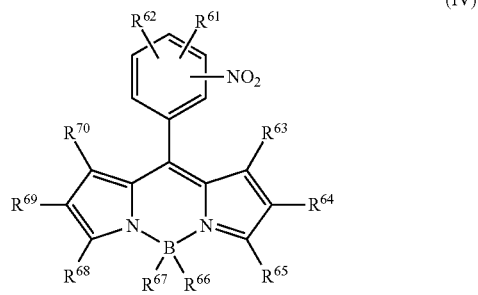

(wherein $R^{61}$ and $R^{62}$ independently represent a $C_{1-8}$ alkoxy group which may be substituted, hydroxy group, an amino group (the amino group may be primary, secondary or tertiary amino group), thiol group or selenol group, provided that both $R^{61}$ and $R^{62}$ do not simultaneously represent a $C_{1-8}$ alkoxy group which may be substituted, $R^{63}$, $R^{65}$, $R^{68}$ and $R^{70}$ represent a $C_{1-8}$ alkyl group which may be substituted, $R^{64}$ and $R^{69}$ represent an electron withdrawing group selected from the group consisting of cyano group, carboxy group and an alkyloxycarbonyl group which may be substituted, and $R^{66}$ and $R^{67}$ independently represent a halogen atom, a $C_{1-8}$ alkyl group which may be substituted or a $C_{1-8}$ alkoxy group which may be substituted), or a salt thereof.

According to preferred embodiments of this invention, there are further provided the compound or a salt thereof, wherein, in the aforementioned general formula (IV), $R^{63}$, $R^{65}$, $R^{68}$ and $R^{70}$ are methyl groups, $R^{64}$ and $R^{69}$ are cyano groups, $R^{66}$ and $R^{67}$ are fluorine atoms, $R^{61}$ is hydroxy group, and $R^{62}$ is a $C_{1-8}$ alkoxy group which may be substituted; and the compound or a salt thereof, wherein, in the aforementioned general formula (IV), $R^{63}$, $R^{65}$, $R^{68}$ and $R^{70}$ are methyl groups, $R^{64}$ and $R^{69}$ are cyano groups, $R^{66}$ and $R^{67}$ are fluorine atoms, $R^{61}$ is hydroxy group, and $R^{62}$ is methoxy group, ethoxy group or carboxymethoxy group.

The present invention also provides a method for measuring peroxynitrite, which comprises the following steps:
(a) the step of reacting a compound represented by the aforementioned general formula (I), preferably the aforementioned general formula (II), or a salt thereof with peroxynitrite, and
(b) the step of measuring fluorescence intensity of a compound represented by the aforementioned general formula (III), preferably the aforementioned general formula (IV), produced in the aforementioned step (a).

Further, from another aspect, the present invention provides use of a compound represented by the aforementioned general formula (I) for manufacture of a reagent for measuring peroxynitrite.

BRIEF DESCRIPTION OF THE DRAWINGS

FIG. 1 shows change of fluorescence spectrum observed when peroxynitrite solutions of various concentrations were added to 10 μmol/L of Compound 4 of the present invention obtained in Example 1 of the examples.

FIG. 2 shows change of fluorescence intensity (excitation wavelength: 505 nm, emission wavelength: 518 nm) observed when peroxynitrite solutions were added to make final concentrations of 1, 2, 5, and 10 μmol/L to 10 mmol/L of Compound 4 of the present invention obtained in Example 1 of the examples.

FIG. 3 shows change of fluorescence intensity (excitation wavelength: 505 nm, emission wavelength: 518 nm) observed when peroxynitrite solutions were added to make final concentrations of 0, 1, 2, 5, 10, 20, and 50 μmol/L to 10 μmol/L of Compound 4 of the present invention obtained in Example 1 of the examples.

FIG. 4 shows change of fluorescence spectrum observed when hydrogen peroxide, singlet oxygen, hydroxyl radical, hypochlorite ion, nitrogen monoxide, and peroxynitrite were added to 10 μmol/L of Compound 4 of the present invention obtained in Example 1 of the examples.

FIG. 5 shows results of HPLC analysis of a product obtained by dissolving a 20 mmol/L solution of Compound 4 of the present invention obtained in Example 1 of the examples in DMF at a concentration of 10 μmol/L in 0.1 mol/L phosphate buffer, pH 7.4, and adding a peroxynitrite solution to the solution.

FIG. 6 shows results of LCMS analysis of a product obtained by reacting Compound 4 of the present invention obtained in Example 1 of the examples and peroxynitrite, acidifying the reaction mixture with hydrochloric acid, and extracting the reaction mixture with ethyl acetate.

FIG. 7 shows results of imaging of peroxynitrite using Compound 4 of the present invention obtained in Example 1 of the examples.

BEST MODE FOR CARRYING OUT THE INVENTION

In the aforementioned general formula (I), as the $C_{1-8}$ alkyl group which may be substituted represented by $R^1$, $R^2$, $R^3$, $R^6$, $R^7$ and $R^8$, methyl group, ethyl group and the like are preferred, and as the aryl group which may be substituted represented by $R^1$, $R^2$, $R^3$, $R^6$, $R^7$ and $R^8$, phenyl group is preferred. Examples of the substituent which exists on the vinyl group which may be substituted represented by $R^1$, $R^2$, $R^3$, $R^6$, $R^7$ and $R^8$ include phenyl group, a monoaminophenyl group, a diaminophenyl group (for example, 3,4-diaminophenyl group), and the like. As the thienyl group which may be substituted and the pyrrolyl group which may be substituted represented by $R^1$, $R^2$, $R^3$, $R^6$, $R^7$ and $R^8$, 2-thienyl group and 2-pyrrolyl group are preferred, respectively. When the substituents represented by $R^1$, $R^2$, $R^3$, $R^6$, $R^7$ and $R^8$ are groups other than alkyl group, fluorescence emission wavelength of the compound may shift to longer wavelength side.

In the aforementioned general formula (I), as for the combination of $R^1$, $R^2$, $R^3$, $R^6$, $R^7$ and $R^8$, it is preferred that four of these groups are $C_{1-8}$ alkyl groups which may be substituted, and two of them are electron withdrawing groups selected from the group consisting of cyano group, carboxy group and a $C_{1-8}$ alkyloxycarbonyl group which may be substituted. As the electron withdrawing group, cyano group is preferred. As for the substitution positions of the two electron withdrawing groups, they are preferably $R^2$ and $R^7$. A combination in which $R^1$, $R^3$, $R^6$ and $R^8$ are methyl groups, and $R^2$ and $R^7$ are cyano groups is particularly preferred.

In the aforementioned general formula (I), as the halogen atom represented by $R^4$ and $R^5$, fluorine atom is preferred, as the $C_{1-8}$ alkyl group which may be substituted represented by $R^4$ and $R^5$, methyl group is preferred, and as the $C_{1-8}$ alkoxy group which may be substituted represented by $R^4$ and $R^5$, methoxy group is preferred. As the substituents represented by $R^4$ and $R^5$, fluorine atoms are particularly preferred.

In the group represented by the formula (A), examples of the $C_{1-8}$ alkyl group which may be substituted represented by $R^{11}$, $R^{12}$, $R^{13}$, $R^{14}$ and $R^{15}$ include, for example, a carboxy-substituted $C_{1-8}$ alkyl group, an alkoxycarbonyl-substituted $C_{1-8}$ alkyl group, a sulfo-substituted $C_{1-8}$ alkyl group, an alkyl sulfonate-substituted $C_{1-8}$ alkyl group, and the like. The carboxy-substituted $C_{1-8}$ alkyl group is preferably a monocarboxy-substituted $C_{1-8}$ alkyl group, and carboxymethyl group and the like are preferred. Examples of the alkoxycarbonyl-substituted $C_{1-8}$ alkyl group include a $C_{1-8}$ alkyl ester of the aforementioned monocarboxy-substituted $C_{1-8}$ alkyl group. Preferred are an ethoxycarbonyl-substituted $C_{1-8}$ alkyl group, and the like. The sulfo-substituted $C_{1-8}$ alkyl group is preferably a monosulfo-substituted $C_{1-8}$ alkyl group. As the alkyl sulfonate-substituted $C_{1-8}$ alkyl group, a monoalkyl sulfonate-substituted $C_{1-8}$ alkyl group is preferred. As the alkyl sulfonate group of the alkyl sulfonate-substituted $C_{1-8}$ alkyl group, a $C_{1-8}$ alkyl sulfonate group ($C_{1-8}$ alkyl-O—SO$_2$—) is preferred.

As the $C_{1-8}$ alkoxy group which may be substituted represented by $R^{11}$, $R^{12}$, $R^{13}$, $R^{14}$ and $R^{15}$, a monocarboxy-substituted $C_{1-8}$ alkoxy group and a $C_{1-8}$ alkyl ester group of monocarboxy-substituted $C_{1-8}$ alkoxy group are preferred. Examples of these groups include carboxymethoxy group and the like, and methoxycarbonylmethoxy group and the like, respectively. When the $C_{1-8}$ alkoxy group which may be substituted is a monocarboxy-substituted $C_{1-8}$ alkoxy group, water solubility of the compound may markedly increase, and thus superior effect may be obtained. Further, when the $C_{1-8}$ alkoxy group which may be substituted is a $C_{1-8}$ alkyl ester group of a monocarboxy-substituted $C_{1-8}$ alkoxy group (methoxycarbonylmethoxy group, acetoxymethoxycarbonylmethoxy group, and the like), superior effects may be obtained, for example, cell membrane permeability of the compound increases, and after the compound is incorporated into a cell, the $C_{1-8}$ alkyl ester group is hydrolyzed by intracellular esterase and thereby converted into a highly water-soluble monocarboxy-substituted $C_{1-8}$ alkoxy group to impart cell sustainability to the compound.

As for the combination of the substituents of $R^{11}$, $R^{12}$, $R^{13}$, $R^{14}$ and $R^{15}$, it is preferred that 2 or 3 of these groups are hydrogen atoms, and 2 to 3 of these groups are selected from a $C_{1-8}$ alkoxy group which may be substituted, hydroxy group, an amino group (the amino group may be primary, secondary or tertiary amino group), thiol group and selenol group. It is particularly preferred that three of these groups are hydrogen atoms, and two of these groups are selected from a $C_{1-8}$ alkoxy group which may be substituted, hydroxy group, an amino group (the amino group may be primary, secondary or tertiary amino group), thiol group and selenol group. A particularly preferred combination of the substituents of $R^{11}$, $R^{12}$, $R^{13}$, $R^{14}$ and $R^{15}$ is a combination of hydrogen atoms as three of said groups, hydroxy group, an amino group (the amino group may be primary, secondary or tertiary amino group), thiol group, or selenol group as one of said groups, and a $C_{1-8}$ alkoxy group which may be substituted as one of said groups. The most preferred combination of the substituents of $R^{11}$, $R^{12}$, $R^{13}$, $R^{14}$ and $R^{15}$ is a combination of carboxymethoxy group as $R^{11}$, hydrogen atoms as $R^{12}$, $R^{14}$ and $R^{15}$, and hydroxy group as $R^{13}$.

In the aforementioned general formula (II), $R^{21}$ and $R^{22}$ preferably independently represent a $C_{1-8}$ alkoxy group which may be substituted or hydroxy group (provided that both $R^{21}$ and $R^{22}$ do not simultaneously represent a $C_{1-8}$ alkoxy group which may be substituted), $R^{23}$, $R^{25}$, $R^{28}$ and $R^{30}$ represent a $C_{1-8}$ alkyl group which may be substituted, preferably methyl group or ethyl group, more preferably methyl group, $R^{24}$ and $R^{29}$ are preferably cyano groups, and $R^{26}$ and $R^{27}$ are preferably fluorine atoms.

Types of salts of the compounds represented by the aforementioned general formulas (I) and (II) are not particularly limited, and examples include base addition salts, acid addition salts, amino acid salts, and the like. Examples of the base addition salts include metal salts such as sodium salts, potassium salts, calcium salts and magnesium salts and organic amine salts such as ammonium salts, triethylamine salts, piperidine salts and morpholine salts. Examples of the acid addition salts include mineral acid salts such as hydrochlorides, sulfates and nitrates, and organic acids such as methanesulfonates, paratoluenesulfonates, citrates, and oxalates. Examples of the amino acid salts include glycine salts, and the like. Among them, physiologically acceptable water-soluble salts can be suitably used for the measuring reagent and measurement method of the present invention. Further, the compounds represented by the general formula (I) in free forms and salts thereof may exist as a hydrate or a solvate, and such a hydrate or solvate may be used as the measuring reagent of the present invention. A type of solvent forming the solvate is not particularly limited, and examples thereof include solvents such as ethanol, acetone, isopropanol and the like.

The compounds represented by the general formula (I) may have one or more asymmetric carbon atoms depending on the type of the substituent, and stereoisomers such as optical isomers or diastereoisomers may exist. Any of such stereoisomers in pure forms, arbitrary mixtures of stereoisomers, racemates and the like may be used as the measuring reagent of the present invention.

The compounds represented by the aforementioned general formula (I) and salts thereof have a property of reacting with peroxynitrite under mild conditions, for example, physiological conditions, to produce a compound represented by the general formula (III) wherein one hydrogen atom on the benzene ring in the group represented by the formula (A) is nitrated, or a salt thereof. The compounds represented by the general formula (I) and salts thereof are substantially non-fluorescent, whereas the nitrated compound represented by the general formula (III) and salt thereof have a property of emitting fluorescence of strong intensity. Therefore, peroxynitrite can be measured with high sensitivity by reacting a compound represented by the aforementioned formula (I) or a salt thereof with peroxynitrite and then measuring fluorescence of the nitrated compound represented by the general formula (III) or a salt thereof.

The compounds represented by the aforementioned general formula (I) and salts thereof are characterized in that they do not give fluorescent compounds even if they reacted with the other reactive oxygen species including hydroxyl radical, singlet oxygen, hypochlorite ion, nitrogen monoxide and superoxide which are precursors of peroxynitrite under the aforementioned condition. Therefore, by using a compound represented by the aforementioned general formula (I) or a salt thereof, only peroxynitrite can be specifically measured under physiological condition without being affected by other reactive oxygen species. For example, peroxynitrite localized in individual cells or specific tissue can be accurately and conveniently measured by using a compound represented by the general formula (I) or a salt thereof as a measuring reagent.

The substituents in the general formulas (III) and (IV) are similar to the substituents explained for the general formulas (I) and (II) at the corresponding positions, respectively. Salts and isomers of the compounds of the general formulas (III) and (IV) are also similar to those explained for the compounds of the general formulas (I) and (II). In the group represented by (B) of the compound represented by the general formula (III), position of the nitro group and positions of $R^{51}$, $R^{52}$, $R^{53}$ and $R^{54}$ are not particularly limited, and they can substitute on arbitrary positions on the benzene ring. Further, in the compound represented by the general formula (IV), position of the nitro group substituting on the benzene ring, and positions of $R^{61}$ and $R^{62}$ are not particularly limited, and they can substitute at arbitrary positions on the benzene ring.

The term "measurement" used in the present specification should be construed in the broadest sense thereof including determinations, tests, detections and the like performed for the purpose of quantitative analysis, qualitative analysis, diagnosis or the like. The method for measuring peroxynitrite of the present invention generally comprises (A) the step of reacting a compound represented by the aforementioned general formula (I) or a salt thereof with peroxynitrite, and (B) the steps of measuring fluorescence of a nitro compound represented by the general formula (III) or a salt thereof produced in the aforementioned step (A).

Fluorescence of the nitrated compound represented by the general formula (III) or a salt thereof can be measured by a usual method, and a method of measuring fluorescence spectra in vitro, a method of measuring fluorescence spectra in vivo using a bioimaging technique, or the like can be used. For example, when quantitative analysis is performed, it is desirable to create a calibration curve beforehand in a conventional manner. The measuring reagent of the present invention has a property of being easily taken up in a cell, and thus peroxynitrite localized in individual cells can be measured by a bioimaging technique with high sensitivity.

As the measuring reagent of the present invention, a compound represented by the aforementioned general formula (I) or a salt thereof per se may be used. The compounds may be added with additives usually used for preparation of reagents and used as a composition. For example, additives such as dissolving aids, pH modifiers, buffers and isotonic agents can be used as the additive for using the reagent in a physiological environment. An amount of each of these additives can be suitably selected by those skilled in the art. Such a composition is provided as a composition in an arbitrary form such as powdery mixture, lyophilized product, granule, tablet and solution.

Methods for preparing typical compounds among the compounds of the present invention are specifically shown in the examples of this specification. Therefore, those skilled in the art can prepare each of the compounds of the present invention represented by the aforementioned general formula (I) by suitably choosing starting materials, reaction conditions, reagents, and the like on the basis of those explanations, and adding modification or alteration to those methods as required. As for the indacene structure, synthesis methods are mentioned in, for example, Japanese Patent Unexamined Publication (KOKAI) Nos. 10-338695 and 11-5796, New J. Chem., 25, pp. 289-292, 2001; Tetrahedron Letters, 42, pp. 6711-6713, 2001; Angew. Chem. Int. Ed., 40, pp. 385-387, 2001; Japanese Patent Laid-Open Publication (KOKAI) No. 2003-277385, and the like. Therefore, those skilled in the art can still more easily prepare the compounds of the present invention by referring to these publications. The entire disclosures of the aforementioned publications are incorporated into the disclosure of this specification by reference.

EXAMPLES

Hereafter, the present invention will be explained more specifically by referring to examples. However, the scope of the present invention is not limited to the examples.

Example 1

Synthesis of Peroxynitrite Fluorescent Probe

The synthetic scheme of Compound 4 is shown below.

[Formula 7]

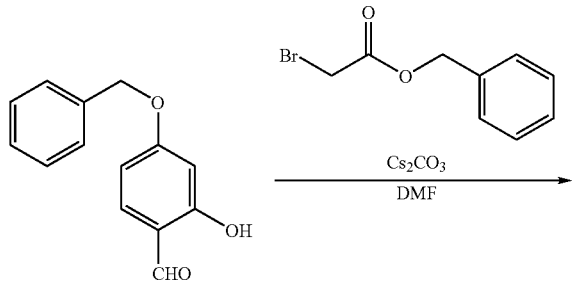

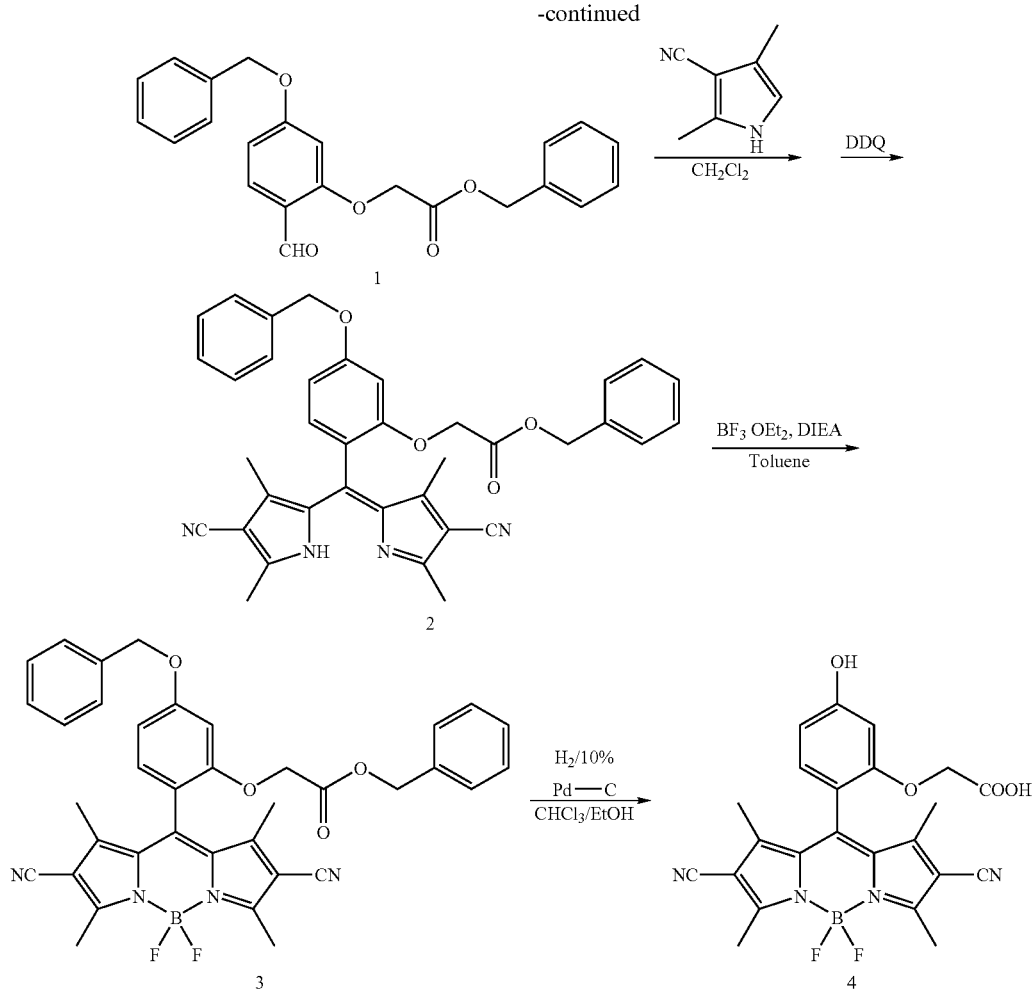

(a) Synthesis of 3-cyano-2,4-dimethylpyrrole

Synthesis was performed according to the method described in known literature (Australian Journal of Chemistry, 17, pp. 1013-1021, 1965).

(b) Synthesis of Compound 1 (4-benzyloxy-2-benzyloxycarbonylmethoxybenzaldehyde)

4-Benzyloxy-2-hydroxybenzaldehyde (1 g, 4.39 mmol) was dissolved in distilled dimethylformamide (DMF, 8 mL), the solution was added with benzyl bromoacetate (1.1 g, 4.82 mmol) and cesium carbonate (1.57 g, 4.83 mmol), and the mixture was stirred overnight at room temperature under an argon atmosphere. The reaction solution was added with water (150 mL), and the mixture was extracted three times with ethyl acetate (100 mL). The extracted organic layer was washed five times with water (50 mL) and once with saturated brine (100 mL), and dried over anhydrous sodium sulfate. The solvent was evaporated under reduced pressure, and the obtained solid was purified by column chromatography (carrier: silica gel 60 N, solvent: dichloromethane), and recrystallized from hexane to obtain the objective compound, Compound 1, as white solid at a yield of 93%.

$^1$H NMR (300 MHz, CDCl$_3$): δ 4.73 (s, 2H), 5.03 (s, 2H), 5.23 (s, 2H), 6.35 (d, J=2.0 Hz, 1H), 6.66 (dd, J=2.0, 8.8 Hz, 1H), 7.33-7.40 (m, 10H), 7.94 (d, J=8.8 Hz, 1H), 10.38 (s, 1H). $^{13}$C NMR (75 MHz, CDCl$_3$): δ 65.4, 67.1, 70.3, 99.6, 107.6, 119.4, 127.5, 128.3, 128.4, 128.6, 128.7, 130.7, 134.8, 135.6, 161.6, 164.9, 167.8, 188.0. MS (ESI$^+$): 399 [M+Na]$^+$.

Anal. Calcd for C$_{23}$H$_{20}$O$_5$: N, 0; C, 73.39; H, 5.36. Found: N, 0; C, 73.18; H, 5.62. Mp: 84.4-85.7° C.

(c) Synthesis of Compound 3 [8-(4-benzyloxy-2-benzyloxycarbonylmethoxyphenyl)-2,6-dicyano-1,3,5,7-tetramethyl-4,4-difluoro-4-bora-3a,4a-diaza-s-indacene]

Compound 1(400 mg, 1.06 mmol) and 3-cyano-2,4-dimethylpyrrole (262 mg, 2.18 mmol) were dissolved in dichloromethane (200 mL), and the mixture was added dropwise with trifluoroacetic acid (2 mL). The mixture was stirred overnight at room temperature, and then added with 2,3-dichloro-5,6-dicyano-p-benzoquinone (314 mg, 1.38 mmol), and the mixture was stirred at room temperature for 30 minutes. The reaction mixture was washed twice with water (100 mL) and once with saturated brine (100 mL), then the solvent was dried over anhydrous sodium sulfate, and concentrated under reduced pressure. The obtained solid was filtered through aluminum oxide by using dichloromethane as a solvent. The solvent was evaporated under reduced pressure to obtain Compounds 2 as a solid crude product. Compound 2 obtained as solid was dissolved in dehydrated toluene (120 mL). This solution was added with diisopropylethylamine (3 mL). And then the mixture was added dropwise with boron trifluoride-diethyl ether complex (2.5 mL), and the mixture was stirred at room temperature for 5 minutes. The reaction mixture was washed twice with water (100 mL) and once with saturated brine (50 mL), and then the solvent was dried over anhydrous sodium sulfate. The solvent was evaporated under reduced pressure, and the residue was purified by column chromatography (carrier: silica gel 60 N, solvent: dichloromethane) to obtain the objective compound, Compound 3 (245 mg, yield: 36%).

$^1$H NMR (300 MHz, CDCl$_3$): 1.54 (s, 6H), 2.70 (s, 6H), 4.61 (s, 2H), 5.05 (s, 2H), 5.17 (s, 2H), 6.42 (d, J=2.0 Hz, 1H), 6.78 (dd, J=2.0, 8.4 Hz, 1H), 7.00 (d, J=8.4 Hz, 1H), 7.31-7.43 (m, 10H). $^{13}$C NMR (75 MHz, CDCl$_3$): 13.4, 13.8, 64.7, 67.4, 70.4, 100.6, 106.0, 108.0, 113.8, 113.9, 127.7, 128.5, 128.6, 128.7, 128.8, 129.4, 132.1, 134.6, 135.7, 144.1, 149.4, 155.0, 159.1, 161.8, 167.7. HRMS (ESI$^-$): calcd for [M-H]$^-$, 643.2328; Found, 643.2334. Anal. Calcd for C$_{37}$H$_{31}$BF$_2$N$_4$O$_4$: N, 8.69; C, 68.95; H, 4.85. Found: N, 8.39; C, 68.71; H, 5.02.

(d) Synthesis of Compound 4 [2,6-dicyano-8-(4-hydroxy-2-carboxymethoxyphenyl)-1,3,5,7-tetramethyl-4,4-difluoro-4-bora-3a,4a-diaza-s-indacene]

Compound 3 (35 mg) was dissolved in chloroform (10 mL), and the solution was diluted with ethanol (40 mL). This solution was added with a small amount of 10% Pd—C, and the mixture was vigorously stirred overnight under a hydrogen atmosphere. The reaction mixture was filtered, the solvent was evaporated under reduced pressure, and then the residue was purified by column chromatography (carrier: silica gel 60, solvent: 9% methanol/dichloromethane) to obtain the objective compound, Compound 4 (15 mg, yield: 59%).

$^1$H NMR (300 MHz, CDCl$_3$): 1.75 (s, 6H), 2.71 (s, 6H), 4.61 (s, 2H), 6.44 (d, J=1.6 Hz, 1H), 6.68 (dd, J=1.6, 8.2 Hz, 1H), 6.93 (d, J=8.2 Hz, 1H). HRMS HRMS (ESI$^-$): calcd for [M-H]$^-$, 463.1389; found 463.1342

Example 2

Reaction of Compound 4 and Peroxynitrite

A 10 μmol/L solution of Compound 4 was prepared by diluting a 20 mmol/L solution of Compound 4 in DMF with a 100 mmol/L phosphate buffer (pH 7.4). The solution was added with peroxynitrite solutions of 2 mmol/L, 5 mmol/L, 10 mmol/L, 20 mmol/L and 80 mmol/L at peroxynitrite final concentrations of 1, 2, 4, 5, 10, 20 or 50 μmol/L with stirring, and after 60 seconds, fluorescence spectrum was measured (excitation wavelength: 505 nm). The results are shown in FIGS. 1, 2 and 3. As clearly seen from the results shown in FIGS. 1, 2 and 3, peroxynitrite addition amount-dependent increase in fluorescence intensity was observed (maximum fluorescence wavelength: 518 nm), and therefore it was demonstrated that Compound 4 of the present invention emitted fluorescence by a reaction with peroxynitrite in a peroxynitrite concentration-dependent manner.

Example 3

Reaction of Compound 4 and Various Reactive Oxygen Species

A 10 μmol/L solution of Compound 4 was prepared by diluting a 20 mmol/L solution of Compound 4 in DMF with a 100 mmol/L phosphate buffer (pH 7.4), and used for the test. The prepared solution was treated under the following conditions for 3 minutes (except for (f), for which treatment time was 30 minutes).

(a) Peroxynitrite was added to make a final concentration of 10 μmol/L.

(b) Hydrogen peroxide was added to make a final concentration of 1 mmol/L.

(c) Hydrogen peroxide and hypochlorite ions were added to make final concentrations of 1 mmol/L and 100 μmol/L, respectively.

(d) Hydrogen peroxide and iron(II) sulfate were added to make final concentrations of 1 mmol/L and 50 μmol/L, respectively.

(e) Hypochlorite ions were added to make a final concentration of 10 μmol/L.

(f) NOC-13 (nitrogen monoxide discharging agent, Dojindo Laboratory) was added to make a final concentration of 100 μmol/L.

After the reaction, change of fluorescence spectrum under each condition was measured to compare reactivities of the compound with (#2) peroxynitrite, (#3) hydrogen peroxide, (#4) singlet oxygen, (#5) hydroxyl radical, (#6) hypochlorite ion, and (#7) nitrogen monoxide. The results are shown in FIG. 4. As clearly seen from the results shown in FIG. 4, it was confirmed that Compound 4 of the present invention did not emit fluorescence at all with addition of hydrogen peroxide, singlet oxygen, hydroxyl radical, hypochlorite ion or nitrogen monoxide, but emitted intense fluorescence after addition of peroxynitrite. It was thus demonstrated that Compound 4 of the present invention had high selectivity to peroxynitrite.

Example 4

Confirmation of Reaction Product Obtained from Compound 4 and Peroxynitrite

A 20 mmol/L solution of the compound of the present invention obtained in Example 1 in DMF was dissolved in a 0.1 mol/L phosphate buffer, pH 7.4, at a concentration of 10 μmol/L, the solution was added with a peroxynitrite solution, and then the reaction mixture was analyzed by HPLC. The results are shown in FIG. 5. The results of the HPLC analysis are shown for the samples (A) before the reaction, (B) after addition of peroxynitrite at a final concentration of 10 μmol/L, and (C) after addition of peroxynitrite at a final concentration of 50 μmol/L, respectively. In the graphs, the lower curves represent the analytical results obtained on the basis of absorbance at 500 nm, and the upper curves represent the analysis results obtained on the basis of fluorescence intensity at 520 nm (excitation: 500 nm).

Analysis Conditions

Column: GL Science Inc., Inertsil ODS-3, 5 μm 4.6×250 mm
Flow Rate: 1 mL/min
Elution solution A: 0.1% Aqueous trifluoroacetic acid
Elution solution B: 80% Aqueous acetonitrile (added with 0.1% trifluoroacetic acid)
Gradient: A/B=60/40=>0/100 (10 minutes)

When the HPLC analysis was performed without addition of peroxynitrite, only the peak of non-fluorescent Compound 4 having absorbance at 500 nm was observed at 11.1-minutes (A). Whilst, in the HPLC analysis after adding peroxynitrite, generation of a fluorescent peak considered to be of a reaction product with peroxynitrite was observed at 11.9-minutes (B, C). Further, a product obtained by reacting Compound 4 and peroxynitrite in a cuvette, then making the reaction mixture acidic with 1 N hydrochloric acid, and then extracting the reaction mixture with ethyl acetate was analyzed by LCMS.

Analysis Conditions

Column: GL Science Inc., Inertsil ODS-3, 5 μm 2.1×150 mm
Flow Rate: 0.2 mL/min
Elution solution A: 0.1% Aqueous formic acid Elution solution B: 80% Aqueous acetonitrile (added with 0.1% trifluoroacetic acid)
Gradient: A/B=60/40=>0/100 (10 minutes)

The results are shown in FIG. 6. A peak of Compound 4 having a mass of 463 ([M-H]$^-$) was observed at 13.1 minutes, and a peak of a mass of 508 was observed at 15.1 minutes. The peak of a mass of 508 at 15.1 minutes showed agreement with HRMS [M-H]$^-$ analysis result of a nitrated compound separately synthesized according to the following scheme (calcd. for [M-H]$^-$: 508.1239, Found: 508.1214) within an measurement error. On the basis of the above results, it was demonstrated that Compound 4 of the present invention reacted with peroxynitrite and became a compound in which hydrogen atom on the benzene ring was replaced with nitro group.

[Formula 8]

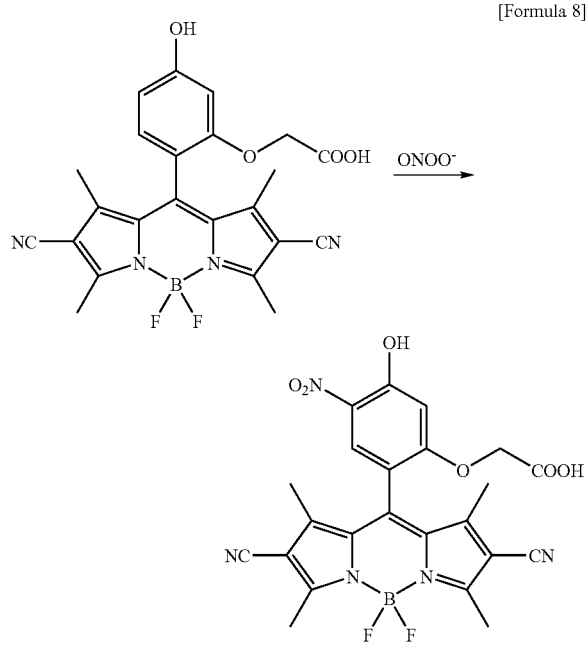

Example 5

Imaging of Peroxynitrite Using Compound 4

HeLa cells were precultured in Dulbecco's modified Eagle's medium (DMEM) supplemented with 10% (v/v) fetal bovine serum, penicillin (100 units/mL), and streptomycin (100 μg/mL) in a 5% $CO_2$ incubator. These HeLa cells were inoculated on a 35 mm glass bottom dish (MatTek Corporation), and further cultured overnight in DMEM. After 24 hours, the medium was removed, and the HeLa cells were washed with Hank's balanced salt solution (HBSS, 2×1 mL). The HeLa cells were added with 2 mL of 2 μmol/L solution of Compound 4 in HBSS (containing 0.01% DMF and 0.01% Cremophor EL (SIGMA) as auxiliary solvents), and incubated at room temperature for 20 minutes. Then, the HeLa cells were washed with HBSS (2×1 mL). Fluorescence images before addition of peroxynitrite and after addition of peroxynitrite at a final concentration of 10 μmol/L were photographed at an excitation wavelength of 470 to 490 nm and fluorescence emission wavelength of 510 to 550 nm.

The results are shown in FIG. 7. Among the photographs, (A) is a differential interference microscope image of HeLa cells loaded with Compound 4, (B) is a pseudo color fluorescence image of fluorescence intensity before addition of peroxynitrite, (C) is a pseudo color fluorescence image of fluorescence intensity after addition of peroxynitrite, and (D) is a fused image of (A) and (B). As clearly seen from (B) and (C), fluorescence imaging of peroxynitrite was performable by using the compound of the present invention.

INDUSTRIAL APPLICABILITY

The compounds of the present invention are useful as fluorescent probes capable of highly selectively measuring peroxynitrite, in particular, useful as peroxynitrite-highly-selective fluorescent probes applicable to bioimaging methods.

What is claimed is:
1. A compound represented by the following general formula (I) or a salt thereof:

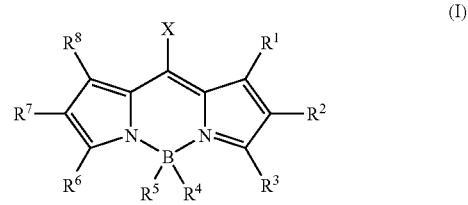

wherein $R^1$, $R^3$, $R^6$ and $R^8$ independently represent a hydrogen atom, a $C_{1-8}$ alkyl group which may be substituted, an aryl group which may be substituted, a vinyl group which may be substituted, a thienyl group which may be substituted, or a pyrrolyl group which may be substituted, or represent an electron withdrawing group selected from a cyano group, a carboxy group, and an alkyloxycarbonyl group which may be substituted, $R^2$ and $R^7$ each represent a cyano group, $R^4$ and $R^5$ independently represent a halogen atom, a $C_{1-8}$ alkyl group which may be substituted, or a $C_{1-8}$ alkoxy group which may be substituted, and X represents a group represented by the following formula (A):

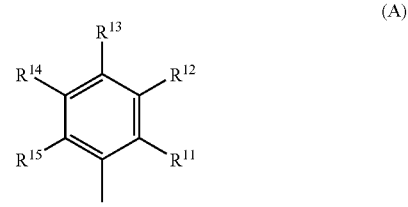

wherein $R^{11}$, $R^{12}$, $R^{13}$, $R^{14}$ and $R^{15}$ independently represent a hydrogen atom, a $C_{1-8}$ alkyl group which may be substituted, a $C_{1-8}$ alkoxy group which may be substituted, a hydroxy group, an amino group, wherein the amino group comprises a primary, secondary or tertiary amino group, a thiol group or a selenol group, provided that 2 to 3 groups among $R^{11}$, $R^{12}$, $R^{13}$, $R^{14}$ and $R^{15}$ represent a $C_{1-8}$ alkoxy group which may be substituted, a hydroxy group, an amino group, wherein the amino group comprises a primary, secondary or tertiary amino group, a thiol group or a selenol group, but all the groups do not simultaneously represent a $C_{1-8}$ alkoxy group which may be substituted, wherein the compound represented by the formula (I) or a salt thereof is non-fluorescent before reacting with peroxynitrite, and the compound represented by the formula (I) or a salt thereof is fluorescent when the group represented by the formula (A) is nitrated after reacting with peroxynitrite.

2. The compound or a salt thereof according to claim 1, wherein $R^1$, $R^3$, $R^6$ and $R^8$ are methyl groups, $R^4$ and $R^5$ are fluorine atoms, and X is a group represented by the aforementioned formula (A), wherein the substituents have the same meanings as those defined above.

3. A compound represented by the following general formula (II):

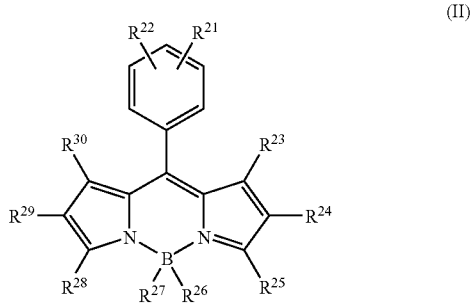

(II)

wherein $R^{21}$ and $R^{22}$ independently represent a $C_{1-8}$ alkoxy group which may be substituted, a hydroxy group, an amino group, wherein the amino group comprises a primary, secondary or tertiary amino group, a thiol group or a selenol group, provided that both $R^{21}$ and $R^{22}$ do not simultaneously represent a $C_{1-8}$ alkoxy group which may be substituted, $R^{23}$, $R^{25}$, $R^{28}$ and $R^{30}$ represent a $C_{1-8}$ alkyl group which may be substituted, $R^{24}$ and $R^{29}$ each represent a cyano group $R^{26}$ and $R^{27}$ independently represent a halogen atom, a $C_{1-8}$ alkyl group which may be substituted, or a $C_{1-8}$ alkoxy group which may be substituted, or a salt thereof, wherein the compound represented by the formula (II) or a salt thereof is non-fluorescent before reacting with peroxynitrite, and the compound represented by the formula (II) or a salt thereof is fluorescent when the benzene ring to which $R^{21}$ and $R^{22}$ bind is nitrated after reacting with peroxynitrite.

4. The compound or a salt thereof according to claim 3, wherein $R^{21}$ and $R^{22}$ consist of a combination of hydroxy group and a $C_{1-8}$ alkoxy group which may be substituted, $R^{23}$, $R^{25}$, $R^{28}$ and $R^{30}$ are $C_{1-8}$ alkyl groups which may be substituted, nd $R^{26}$ and $R^{27}$ are fluorine atoms.

5. The compound or a salt thereof according to claim 3, wherein $R^{21}$ and $R^{22}$ consist of a combination of a hydroxy group and a mono-carboxy group-substituted $C_{1-4}$ alkoxy group, $R^{23}$, $R^{25}$, $R^{28}$ and $R^{30}$ are $C_{1-4}$ alkyl groups, and $R^{26}$ and $R^{27}$ are fluorine atoms.

6. A compound represented by the following general formula (III) or a salt thereof:

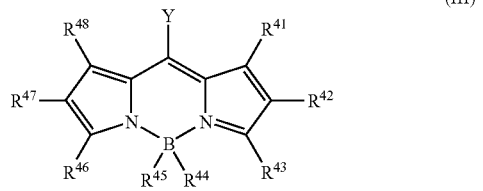

(III)

wherein $R^{41}$, $R^{43}$, $R^{46}$ and $R^{48}$ independently represent a hydrogen atom, a $C_{1-8}$ alkyl group which may be substituted, an aryl group which may be substituted, a vinyl group which may be substituted, a thienyl group which may be substituted, or a pyrrolyl group which may be substituted, or represent an electron withdrawing group selected from a cyano group, a carboxy group, and an alkyloxycarbonyl group which may be substituted, $R^{42}$ and $R^{47}$ each represent a cyano group, $R^{44}$ and $R^{45}$ independently represent a halogen atom, a $C_{1-8}$ alkyl group which may be substituted, or a $C_{1-8}$ alkoxy group which may be substituted, and Y represents a group represented by the following formula (B):

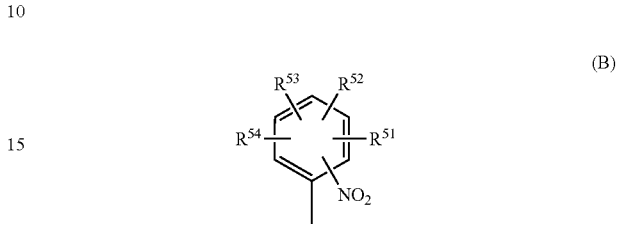

(B)

wherein $R^{51}$, $R^{52}$, $R^{53}$ and $R^{54}$ independently represent a hydrogen atom, a halogen atom, a $C_{1-8}$ alkyl group which may be substituted, a $C_{1-8}$ alkoxy group which may be substituted, a hydroxy group, an amino group, wherein the amino group comprises a primary, secondary or tertiary amino group, a thiol group or a selenol group, provided that 2 to 3 groups among $R^{51}$, $R^{52}$, $R^{53}$ and $R^{54}$ represent a $C_{1-8}$ alkoxy group which may be substituted, a hydroxy group, an amino group, wherein the amino group comprises a primary, secondary or tertiary amino group, a thiol group or a selenol group, but all the groups do not simultaneously represent a $C_{1-8}$ alkoxy group which may be substituted, wherein the compound represented by the formula (III) or a salt thereof is fluorescent.

7. The compound or a salt thereof according to claim 6, wherein $R^{41}$, $R^{43}$, $R^{46}$ and $R^{48}$ are methyl groups, $R^{44}$ and $R^{45}$ are fluorine atoms, and Y is a group represented by the formula (B), wherein in the formula (B), $R^{51}$ is a $C_{1-8}$ alkoxy group which may be substituted, $R^{52}$ and $R^{53}$ are hydrogen atoms, and $R^{54}$ is hydroxy group.

8. A compound represented by the following general formula (IV):

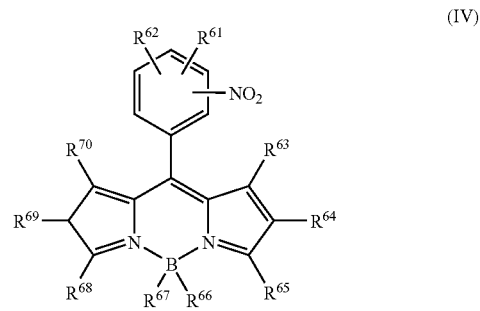

(IV)

wherein $R^{61}$ and $R^{62}$ independently represent a $C_{1-8}$ alkoxy group which may be substituted, a hydroxy group, an amino group, wherein the amino group comprises a primary, secondary or tertiary amino group, a thiol group or a selenol group, provided that both $R^{61}$ and $R^{62}$ do not simultaneously represent a $C_{1-8}$ alkoxy group which may be substituted, $R^{63}$, $R^{65}$, $R^{68}$ and $R^{70}$ represent a $C_{1-8}$ alkyl group which may be substituted, $R^{64}$ and $R^{69}$ each represent a cyano group, and $R^{66}$ and $R^{67}$ independently represent a halogen atom, a $C_{1-8}$ alkyl group which may be substituted or a $C_{1-8}$ alkoxy group which may be substituted, or a salt thereof, wherein the compound represented by the formula (IV) or a salt thereof is fluorescent.

9. The compound or a salt thereof according to claim 8, wherein $R^{63}$, $R^{65}$, $R^{68}$ and $R^{70}$ are methyl groups, $R^{66}$ and $R^{67}$ are fluorine atoms, $R^{61}$ is hydroxy group, and $R^{62}$ is a $C_{1-8}$ alkoxy group which may be substituted.

10. The compound or a salt thereof according to claim 8, wherein $R^{63}$, $R^{65}$, $R^{68}$ and $R^{70}$ are methyl groups, $R^{66}$ and $R^{67}$ are fluorine atoms, $R^{61}$ is a hydroxy group, and $R^{62}$ is a methoxy group, an ethoxy group, or a carboxymethoxy group.

11. A method for measuring peroxynitrite, which comprises the following:
   (a) reacting a compound represented by the following general formula (I) or a salt thereof and peroxynitrite:

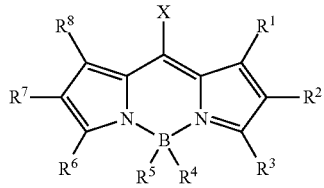

(I)

wherein $R^1$, $R^3$, $R^6$ and $R^8$ independently represent a hydrogen atom, a $C_{1-8}$ alkyl group which may be substituted, an aryl group which may be substituted, a vinyl group which may be substituted, a thienyl group which may be substituted, or a pyrrolyl group which may be substituted, or represent an electron withdrawing group selected from a cyano group, a carboxy group, and an alkyloxycarbonyl group which may be substituted, $R^2$ and $R^7$ each represent a cyano group, $R^4$ and $R^5$ independently represent a halogen atom, a $C_{1-8}$ alkyl group which may be substituted, or a $C_{1-8}$ alkoxy group which may be substituted, and X represents a group represented by the following formula (A):

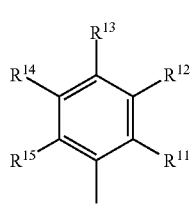

(A)

wherein $R^{11}$, $R^{12}$, $R^{13}$, $R^{14}$ and $R^{15}$ independently represent a hydrogen atom, a $C_{1-8}$ alkyl group which may be substituted, a $C_{1-8}$ alkoxy group which may be substituted, a hydroxy group, an amino group, wherein the amino group comprises a primary, secondary or tertiary amino group, a thiol group or a selenol group, provided that 2 to 3 groups among $R^{11}$, $R^{12}$, $R^{13}$, $R^{14}$ and $R^{15}$ represent a $C_{1-8}$ alkoxy group which may be substituted, a hydroxy group, an amino group, wherein the amino group comprises a primary, secondary or tertiary amino group, a thiol group or a selenol group, but all the groups do not simultaneously represent a $C_{1-8}$ alkoxy group which may be substituted, wherein the compound represented by the formula (I) or a salt thereof is non-fluorescent before reacting with peroxynitrite, and the compound represented by the formula (I) or a salt thereof is fluorescent when the group represented by the formula (A) is nitrated after reacting with peroxynitrite, and
   (b) measuring fluorescence intensity of a compound or a salt thereof represented by the following general formula (III) produced in the aforementioned (a):

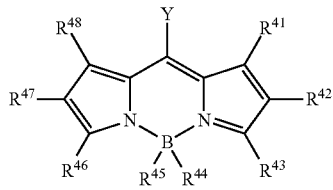

(III)

wherein $R^{41}$, $R^{43}$, $R^{46}$ and $R^{48}$ independently represent a hydrogen atom, a $C_{1-8}$ alkyl group which may be substituted, an aryl group which may be substituted, a vinyl group which may be substituted, a thienyl group which may be substituted, or a pyrrolyl group which may be substituted, or represent an electron withdrawing group selected from a cyano group, a carboxy group, and an alkyloxycarbonyl group which may be substituted, $R^{42}$ and $R^{47}$ each represent a cyano group, $R^{44}$ and $R^{45}$ independently represent a halogen atom, a $C_{1-8}$ alkyl group which may be substituted, or a $C_{1-8}$ alkoxy group which may be substituted, and Y represents a group represented by the following formula (B):

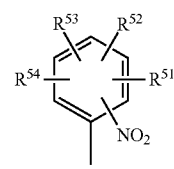

(B)

wherein $R^{51}$, $R^{52}$, $R^{53}$ and $R^{54}$ independently represent a hydrogen atom, a halogen atom, a $C_{1-8}$ alkyl group which may be substituted, a $C_{1-8}$ alkoxy group which may be substituted, a hydroxy group, an amino group, wherein the amino group comprises a primary, secondary or tertiary amino group, a thiol group or a selenol group, provided that 2 to 3 groups among $R^{51}$, $R^{52}$, $R^{53}$ and $R^{54}$ represent a $C_{1-8}$ alkoxy group which may be substituted, a hydroxy group, an amino group, wherein the amino group comprises a primary, secondary or tertiary amino group, a thiol group or a selenol group, but all the groups do not simultaneously represent a $C_{1-8}$ alkoxy group which may be substituted, wherein the compound represented by the formula (III) or the salt thereof is fluorescent.

12. The compound or salt thereof according to claim 1 which is 2,6-dicyano-8-(4-hydroxy-2-carboxymethoxyphenyl)-1,3,5,7-tetramethyl-4,4-difluoro-4-bora-3a,4a-diaza-s-indacene.

* * * * *